United States Patent
Kärkelä et al.

(10) Patent No.: US 11,846,575 B2
(45) Date of Patent: Dec. 19, 2023

(54) SAMPLING ARRANGEMENT

(71) Applicant: TEKNOLOGIAN TUTKIMUSKESKUS VTT OY, Espoo (FI)

(72) Inventors: Teemu Kärkelä, VTT (FI); Jouni Hokkinen, VTT (FI)

(73) Assignee: TEKNOLOGIAN TUTKIMUSKESKUS VTT OY, Espoo (FI)

( * ) Notice: Subject to any disclaimer, the term of this patent is extended or adjusted under 35 U.S.C. 154(b) by 214 days.

(21) Appl. No.: 17/419,341

(22) PCT Filed: Dec. 18, 2019

(86) PCT No.: PCT/FI2019/050903
§ 371 (c)(1),
(2) Date: Jun. 29, 2021

(87) PCT Pub. No.: WO2020/141250
PCT Pub. Date: Jul. 9, 2020

(65) Prior Publication Data
US 2022/0082477 A1    Mar. 17, 2022

(30) Foreign Application Priority Data

Dec. 31, 2018 (FI) .................... 20186140

(51) Int. Cl.
*G01N 1/22* (2006.01)
*G01N 1/40* (2006.01)
*G01N 33/00* (2006.01)

(52) U.S. Cl.
CPC ....... *G01N 1/2273* (2013.01); *G01N 33/0011* (2013.01); *G01N 33/0073* (2013.01);
(Continued)

(58) Field of Classification Search
CPC ............ G01N 1/2273; G01N 33/0011; G01N 33/0073; G01N 1/4022; G01N 2001/2282;
(Continued)

(56) References Cited

U.S. PATENT DOCUMENTS 2,089,558 A    8/1937    Karwat
2,571,014 A    10/1951   Colburn et al.
(Continued)

FOREIGN PATENT DOCUMENTS

CN    102004134 A    4/2011
CN    103920303 A    7/2014
(Continued)

OTHER PUBLICATIONS

CN-107976342-A-English (Year: 2018).*
(Continued)

*Primary Examiner* — Kristina M Deherrera
*Assistant Examiner* — Fatemeh Esfandiari Nia
(74) *Attorney, Agent, or Firm* — Robert P. Michal, Esq.; Carter, DeLuca & Farrell LLP

(57) ABSTRACT

A sampling arrangement includes a sample concentration element configured to trap at least one analyte of interest by freezing; and a sample release arrangement configured to provide a flow of gas, at room temperature on or around the sample concentration element in order to change the temperature thereof; wherein the sample release arrangement further includes a release gas preprocessing element; and a pump element configured to provide the gas flow on or around the sample concentration element.

15 Claims, 2 Drawing Sheets

(52) U.S. Cl.
CPC ... *G01N 1/4022* (2013.01); *G01N 2001/2282* (2013.01); *G01N 2001/4033* (2013.01)

(58) Field of Classification Search
CPC ... G01N 2001/4033; G01N 2001/4027; G01N 2001/225; G01N 1/02; G01N 1/22; G01N 1/2202; G01N 1/2247; G01N 1/2252; G01N 1/405; G01N 1/40; G01N 1/42
See application file for complete search history.

(56) References Cited

U.S. PATENT DOCUMENTS

| | | | |
|---|---|---|---|
| 3,093,470 A | 6/1963 | Melikian et al. | |
| 3,103,427 A | 9/1963 | Jennings | |
| 3,418,820 A | 12/1968 | Swearingen | |
| 4,530,250 A | 7/1985 | Gay et al. | |
| 4,679,401 A | 7/1987 | Lessard et al. | |
| 5,563,352 A * | 10/1996 | Helmig | G01N 30/12 73/23.41 |
| 6,277,649 B1 | 8/2001 | Markelov | |
| 2007/0151326 A1 | 7/2007 | Kim et al. | |
| 2011/0048068 A1 | 3/2011 | Valor Herencia et al. | |
| 2011/0283737 A1 | 11/2011 | Alvord et al. | |
| 2016/0258429 A1 * | 9/2016 | Oikawa | F04B 37/08 |
| 2016/0363513 A1 | 12/2016 | Kossakovski et al. | |
| 2019/0265205 A1 * | 8/2019 | Spartz | G01N 1/4022 |

FOREIGN PATENT DOCUMENTS

| | | | | |
|---|---|---|---|---|
| CN | 205317559 U | * | 6/2016 | |
| CN | 107976342 A | * | 5/2018 | B01D 53/346 |
| CN | 107976342 A | | 5/2018 | |
| JP | 663285278 A | | 11/1988 | |
| JP | 6351525 B2 | | 7/2018 | |

OTHER PUBLICATIONS

CN-205317559-U-English (Year: 2016).*
Office Action issued by the Finnish Patent and Registration Office in relation to Finnish Application No. 20186140 dated Apr. 27, 2022 (7 pages).
Harynuk J et al: "New liquid nitrogen cryogenic modulator for comprehensive two-dimensional gas chromatography", Journal of Chromatography A, Elsevier, Amsterdam, NL, vol. 1019, No. 1-2, Nov. 26, 2003 (Nov. 26, 2003), pp. 53-63.
"Real-time analysis of 13C- and D-CH4 in ambient air with laser spectroscopy: method development and first intercomparison results", Eyer et al., Atmos. Meas. Tech., 9, 263-280, 2016.
International Search Report issued by the European Patent Office acting as the International Searching Authority in relation to International Application No. PCT/FI2019/050903 dated Apr. 8, 2020 (4 pages).
Written Opinion of the International Searching Authority issued by the European Patent Office acting as the International Searching Authority in relation to International Application No. PCT/FI2019/050903 dated Apr. 8, 2020 (5 pages).
Finnish Search Report issued by the Finnish Patent and Registration Office in relation to Finnish Application No. 20186140 dated Jul. 7, 2019 (2 pages).
Finnish Office Action issued by the Finnish Patent and Registration Office in relation to Finnish Application No. 20186140 dated Jul. 10, 2019 (5 pages).

* cited by examiner

SAMPLING ARRANGEMENT

CROSS-REFERENCE TO RELATED APPLICATIONS

This application is a national phase entry under 35 U.S.C. 371 of PCT International Application No. PCT/FI2019/050903 filed Dec. 18, 2019, which claims priority to Finnish Patent Application No. 20186140, filed Dec. 31, 2018, the disclosure of each of these applications is expressly incorporated herein by reference in their entirety.

TECHNICAL FIELD

The present application generally relates to sampling. In particular, but not exclusively, the present application relates to sampling analytes in gaseous form. In particular, but not exclusively, the present application relates to trapping and releasing an analyte in gaseous form.

BACKGROUND

This section illustrates useful background information without admission of any technique described herein being representative of the state of the art.

Sampling and analyzing an analyte in gaseous form, i.e. gaseous species, often requires specific arrangements for collecting and concentrating the analyte, especially if the concentration of the analyte is low.

Commonly, a sample is extracted from the gas phase by freezing it, for example using a cryotrap. For example, freezing of carbon dioxide $CO_2$ and radiocarbon C-14 bound therewith can be done at temperatures below/colder than about −78.5 degrees Celsius. To be able to analyze the sample concentration, the frozen sample needs to be vaporised. That is normally done using an external resistance heater. Such systems are known e.g. from publication "Real-time analysis of 13C- and D-CH4 in ambient air with laser spectroscopy: method development and first intercomparison results", Eyer et al., Atmos. Meas. Tech., 9, 263-280, 2016 and from publication US20110283737.

However, in existing methods, the resistance heater makes the sampling system complicated with electronics and other mechanics. Furthermore, the resistance heater may also heat-up a cryotrap more than needed and hence the cool-down time may be longer than desired for the sampling frequency. In addition, a stepwise or separated release of the compounds trapped together with the sample is difficult with resistance heater strongly heating the cryotrap. Thus, for example when studying carbon dioxide $CO_2$ containing radiocarbon C-14 in humid outside air, water can be released together with $CO_2$/C-14 and that will lower the accuracy of the further analysis of the released $CO_2$/C-14 with analyser devices.

It is the object of the current invention to provide a sampling arrangement mitigating the problems of the prior art.

SUMMARY

Various aspects of examples of the invention are set out in the claims.

According to a first example aspect of the present invention, there is provided a sampling arrangement, comprising
a sample concentration element configured to trap at least one analyte of interest by freezing; comprising
a sample release arrangement configured to provide a flow of gas, at room temperature on or around the sample concentration element in order to change the temperature thereof; wherein the sample release arrangement comprises a release gas preprocessing element; and a pump element configured to provide the gas flow on or around the sample concentration element.

The release gas preprocessing element may comprise a drying element configured to reduce or remove humidity from the gas flow.

The sample release arrangement may further comprise a flow guide element configured to guide the gas flow on or around the sample concentration element.

The flow guide element may comprise a mantle or a sleeve around the sample concentration element in such a way that a gas flow is guided into the space between the mantle and the sample concentration element.

The sampling arrangement may further comprise a sample preprocessing element.

The sampling arrangement may further comprise a sample inlet element and a sample outlet element connected with the sample concentration element.

The sampling arrangement may further comprise a sample inlet valve and a sample outlet valve upstream and downstream of the sample concentration element, respectively.

According to a second example aspect of the present invention, there is provided a system, comprising the sampling arrangement of the first example aspect of the present invention.

The system may further comprise an analyzer configured to analyze the analyte of interest released from the sample concentration element.

According to a third example aspect of the present invention, there is provided a sampling method, comprising
trapping at least one analyte of interest into a sample concentration element by freezing;
providing a gas flow at room temperature on or around the sample concentration element with a sample release arrangement;
controlling with a control element the gas flow on or around the sample concentration element in such a way as to raise the temperature of the sample concentration element above the freezing point of the analyte of interest so that the analyte of interest is released from the sample concentration element.

Providing the gas flow at room temperature may comprise preprocessing with a release gas preprocessing element.

Preprocessing may comprise removing or reducing humidity from the gas flow.

The method may further comprise conducting a sample comprising the at least one analyte of interest to the sample concentration element from a sample inlet element prior to trapping the at least one analyte of interest.

The method may further comprise preprocessing the sample with a sample preprocessing element.

The method may further comprise conducting the at least one analyte of interest released from the sample concentration element to an analyzer element via a sample outlet element.

Different non-binding example aspects and embodiments of the present invention have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE DRAWINGS

Figure 1:
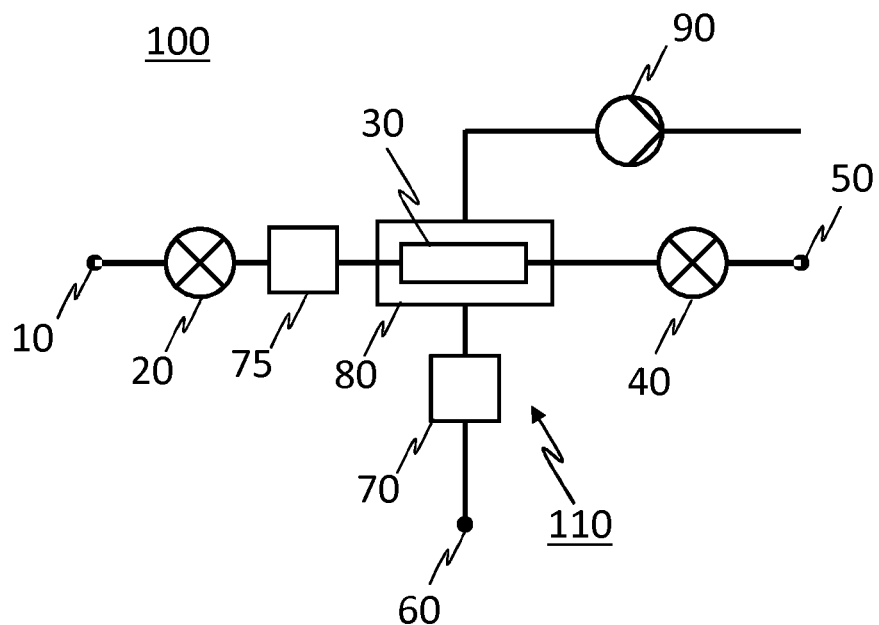
FIG. 1 shows a schematic principle view of a sampling arrangement according to an embodiment of the invention.
Figure 2:
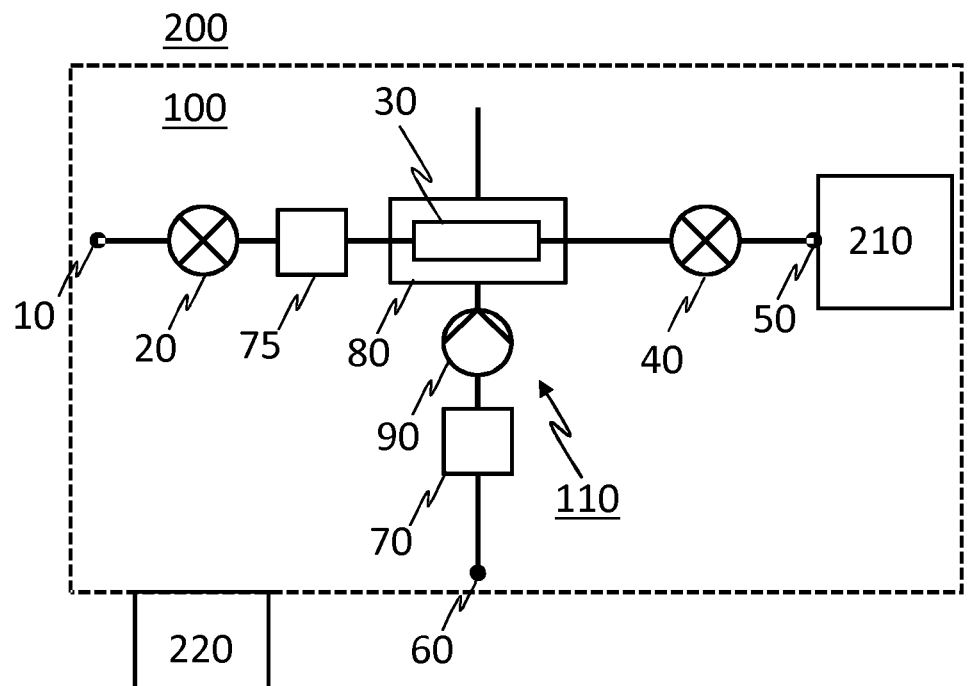
FIG. 2 shows a schematic principle view of a system for sampling and analysis according to an embodiment of the invention.
Figure 3:
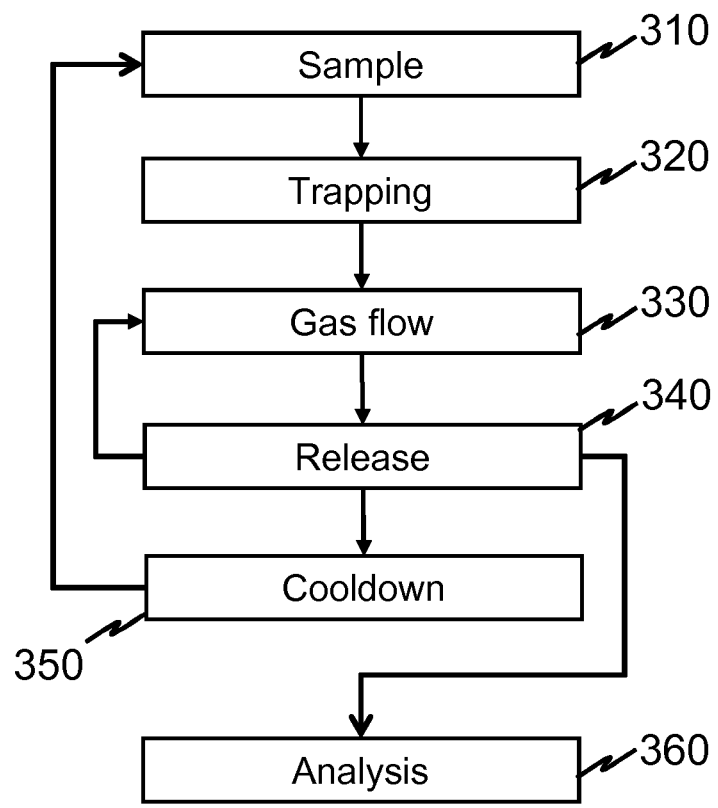
FIG. 3 shows a flowchart of a method for sampling and analysis according to an embodiment of the invention.

The present invention and its potential advantages are understood by referring to FIGS. 1 through 3 of the drawings. In this document, like reference signs denote like parts or steps.

FIG. 1 shows a schematic principle view of a sampling arrangement 100 according to an embodiment of the invention. The sampling arrangement 100 comprises a sample inlet element 10. In an embodiment, the sample inlet element 10 comprises a connector element with which the sampling arrangement is connected to a sample container. In an embodiment, the sample inlet element 10 comprises a connector element with which the sampling arrangement is connected to a source of a gas to be sampled. In a further embodiment, the sample inlet element 10 comprises an inlet open to the surroundings from which the gas is to be sampled.

The sample inlet element 10 is connected, with suitable connectors allowing gas flow, to a sample concentration element 30 configured to trap an analyte of interest. In an embodiment, the sample concentration element 30 is configured to trap an analyte of interest by freezing, i.e. comprises means for freezing an analyte of interest from the sampled gas, i.e. a cooled trap. In an embodiment, the sample concentration element 30 comprises a cryotrap. In an embodiment, the sampling arrangement 100 comprises a sample inlet valve 20 between the sample inlet element 10 and the sample concentration element 30 configured to close the sample inlet flow route. In an embodiment, the sampling arrangement 100 further comprises a sample preprocessing element 75. In an embodiment, the sample preprocessing element 75 comprises a drying element configured to remove or reduce humidity of the sample flow from the sample inlet element 10. In an embodiment, the drying element comprises a chemical absorbent for humidity, such as silica gel or nafion. In an embodiment, the drying element comprises a cold trap. In a further embodiment, the sample preprocessing element 75 comprises a further element, for example a catalytic element, configured to remove a component from the sample flow, such as a component potentially disturbing an analysis of the components of interest. In a still further embodiment, the sample preprocessing element 75 comprises a further drying element, or means for re-routing the gas to the drying element, after removal of a component from the gas flow.

The sampling arrangement 100 further comprises a sample outlet element 50 connected, with suitable connectors allowing gas flow, to the sample concentration element 30. In an embodiment, the sample outlet element 50 comprises a connector element with which the sampling arrangement is connected to analyzing means. In an embodiment, the sampling arrangement 100 comprises a sample outlet valve 40 between the sample outlet element 50 and the sample concentration element 30 configured to close the sample outlet flow route. In a further embodiment, the sampling arrangement comprises pumping means (not shown) for providing a sample flow into the line from the sample inlet element 10 to the ample outlet element 50.

The sampling arrangement 100 further comprises a sample release arrangement 110. The sample release arrangement is configured to change the temperature of the sample concentration element 30 in order to release an analyte therefrom. In an embodiment, the sample release arrangement is configured to provide a flow of gas, at room temperature, such as ambient air, on or around the sample concentration element 30 in order to change the temperature thereof. As the gas flow is provided on or around the sample concentration element 30, and no inside the sampling line, an adequate flow can be easily arranged.

In an embodiment, the sample release arrangement 110 comprises a gas inlet 60. In an embodiment, the gas inlet 60 comprises a valve (not shown) configured to enable closing of the gas inlet. In an embodiment, the gas release arrangement 110 further comprises a release gas preprocessing element 70. In an embodiment, the release gas preprocessing element 70 comprises a drying element configured to remove or reduce humidity of the gas flow from the gas inlet 60. In an embodiment, the drying element comprises a chemical absorbent for humidity, such as silica gel or nafion. In an embodiment, the drying element comprises a cold trap. In a further embodiment, the release gas preprocessing element 70 comprises a further element, for example a catalytic element, configured to remove a component from the gas flow, such as a component potentially disturbing an analysis of the components of interest. In a still further embodiment, the release gas preprocessing element 70 comprises a further drying element, or means for re-routing the gas to the drying element, after removal of a component from the gas flow.

In an embodiment, the gas release arrangement 110 further comprises a flow guide element 80 configured to guide the gas flow on or around the sample concentration element 30 in order to change the temperature thereof. In an embodiment, the flow guide element 80 comprises a mantle or a sleeve around the sample concentration element 30 in such a way that a gas flow is guided into the space between the mantle and the sample concentration element 30. In a further example embodiment, the flow guide element comprises flow guides guiding the flow on or around the sample concentration element. In a further embodiment, no flow guide element 80 needed, put the provided gas flow can simply be directed at or around the sample concentration element directly from the source of the flow, such as a pump.

In an embodiment, the gas release arrangement 110 further comprises a pump element 90 configured to provide a gas flow to the gas release arrangement 110, i.e. to suck gas from the gas inlet 60 through the release gas preprocessing element 70 and provide a gas flow on or around the sample concentration element, in an embodiment, inside the flow guide element 80. FIG. 1 depicts the pump element 90 positioned downstream from the sample concentration element 30 and the flow guide element 80. In a further embodiment, the pump element 90 is positioned upstream of the sample concentration element 30 and the flow guide element 80. In an embodiment, the pump element 90 comprises a vacuum pump.

FIG. 2 shows a schematic principle view of a system 200 for sampling and analysis according to an embodiment of the invention. The system 200 comprises a sampling arrangement 100 as hereinbefore described with reference to FIG. 1.

The system 200 further comprises an analyzer element 210 connected to the sampling arrangement 200. The analyzer element 210 is configured to analyze the sample or samples released from the sample concentration element 30 with the use of the sample release arrangement 110 and conducted into the analyzer via the sample outlet element 50.

The system 200 further comprises a control element 220 configured to control the sampling arrangement 100 and in an embodiment, the analyzer 210. It is to be noted that the control element 220 is in an embodiment integrated with the analyzer element 210, or the sampling arrangement 100 comprises the control element 220 and/or the analyzer element 210 comprises a separate control element.

The control element 220 is configured to control the functions of the system 200 and to cause the system 200 and/or the sampling arrangement 100, which comprises the sample release arrangement 110, to carry out different functions and methods according to embodiments of the invention. In an embodiment, the control element 220 comprises a memory and a processor configured to cause carrying out the various functions of the system 200. IN a further example embodiment, the control element 220 comprises further units, such as a user interface unit and a communication unit. In a still further embodiment, the control element 220 is integrated with an electronic device, such as a personal electronic device or a computer, and connected with system 220 using a suitable interface.

In an embodiment, the control element 220 comprises and/or is connected with various measurement elements (not shown) such as temperature sensors, pressure sensors and flow sensors. In an embodiment, the control element 220 is configured to measure the temperature of the sample concentration element 30, to control the flow of the gas in the sample release arrangement in order to adjust the temperature of the sample concentration element 30, and to control the valves and pumps of the system. In a further embodiment, the control element 220 is configured to measure and/or control the pressure in the sample concentration element.

FIG. 3 shows a flowchart of a method for sampling and analysis according to an embodiment of the invention. All the method hereinafter described are caused to be carried out and controlled by the control element 220. At step 310 the sample is retrieved, i.e. gas that contains the analyte of interest to be sampled and analyzed. The gas to be sample is connected to the sample inlet element 10 of the sampling arrangement 100, for example by opening the sample inlet valve 20 and connecting the sample inlet element to the source of the gas to be sampled.

At step 320 the sample gas, including the analyte or analytes of interest, is trapped into the sample concentration element 30. In an embodiment, the sample gas containing the analyte of interest is preprocessed with a sample preprocessing element 75 prior to trapping. In an embodiment, the sample concentration element 30 comprises a cryotrap and the sample is trapped by lowering the temperature thereof to or below the freezing temperature of the analyte or analytes of interest so that the analytes are trapped into the sample concentration element 30.

At step 330 the sample release arrangement 110 is actuated to provide a flow of gas at room temperature on or around the sample concentration element 30. The flow is conducted via the release gas preprocessing element 70 for example so as to reduce humidity of the room temperature gas in order to avoid condensation of humidity on the surfaces on or near the sample concentration element 30 and/or for removal of components potentially disturbing to the analysis. The flow of room temperature gas is controlled in such a way as to raise the temperature of the sample concentration element above the freezing point of the analyte to be released so that the analyte is released from the trap at step 340 and conducted onwards to the sample outlet element 50 and in an embodiment to the analyzer element 210 to be analyzed at step 360. In an embodiment, simultaneously with the flow of room temperature gas and/or prior or after the flow, the pressure of the sample concentration element 30 is adjusted, for example lowered in order to facilitate the release of the analyte from the sample concentration element 30.

The steps 330 and 340 are in an embodiment repeated in order to first release an analyte with a lower freezing temperature and subsequently a further analyte with a higher freezing temperature. As the flow of room temperature gas used to raise the temperature of the sample concentration element 30 provides for subtle temperature changes, i.e. the raise of temperature is not easily exaggerated, several analytes can be released in controlled manner one after another.

At step 350 the sample concentration element 30 is allowed to cool down and/or the temperature thereof is lowered in a conventional manner. The cooldown can be carried out rapidly, as the flow of room temperature gas used to raise the temperature does not overheat the sample concentration element 30. After cooldown, a further sampling can be carried out starting from step 310.

As an example, the sampling arrangement 100 is used for atmospheric study in air sampling with the analyte of interest being radiocarbon C-14 bound to carbon dioxide $CO_2$. Trapping of $CO_2$/C-14 is carried out by lowering the temperature of the sample concentration element 30, i.e. of a cryotrap, to circa −78.5 degrees of Celsius. The concentrated $CO_2$ is then released by raising the temperature of the sample concentration element 30 with a flow of gas at room temperature. The raising of the temperature can be done quickly and in a precise manner with the raise of temperature being dozens of degrees per minute with a gas flow of circa 10 liter per minute. A further analyte can be released separately, for example water contained in the sampled air can be released after the carbon dioxide.

Without in any way limiting the scope, interpretation, or application of the claims appearing below, a technical effect of one or more of the example embodiments disclosed herein is the provision a quick and accurate release of a frozen analyte. Another technical effect of one or more of the example embodiments disclosed herein is the provision of more subtle heating resulting in a shorter turnaround time for sampling. Another technical effect of one or more of the example embodiments disclosed herein is the provision of a heating enabling release of multiple analytes one after another with reduced risk of crosscontamination.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the foregoing describes example embodiments of the invention, these descriptions should not be viewed in a limiting sense. Rather, there are several variations and modifications which may be made without departing from the scope of the present invention as defined in the appended claims.

The invention claimed is:

1. A sampling arrangement, comprising: a sample concentration element configured to trap at least one analyte of interest by freezing; and a sample release arrangement configured to provide a flow of gas, at room temperature without a heating device, on or around the sample concentration element in order to change the temperature thereof; wherein the sample release arrangement comprises a release gas preprocessing element; and a pump element configured to provide the gas flow on or around the sample concentration element.

2. The sampling arrangement of claim 1, wherein the release gas preprocessing element comprises a drying element configured to reduce or remove humidity from the gas flow.

3. The sampling arrangement of claim 1, wherein the sample release arrangement further comprises a flow guide element configured to guide the gas flow on or around the sample concentration element.

4. The sampling arrangement of claim 3, wherein the flow guide element comprises a mantle or a sleeve around the sample concentration element in such a way that a gas flow is guided into the space between the mantle or the sleeve and the sample concentration element.

5. The sampling arrangement of claim 1, further comprising a sample preprocessing element.

6. The sampling arrangement of claim 1, further comprising a sample inlet element and a sample outlet element connected with the sample concentration element.

7. The sampling arrangement of claim 1, further comprising a sample inlet valve and a sample outlet valve upstream and downstream of the sample concentration element, respectively.

8. A system, comprising the sampling arrangement of claim 1 and a control element.

9. The system of claim 8, further comprising an analyzer configured to analyze the analyte of interest released from the sample concentration element.

10. A sampling method, comprising: trapping at least one analyte of interest into a sample concentration element by freezing; providing a gas flow at room temperature without a heating device on or around the sample concentration element with a sample release arrangement; and controlling with a control element the gas flow on or around the sample concentration element in such a way as to raise the temperature of the sample concentration element above the freezing point of the analyte of interest so that the analyte of interest is released from the sample concentration element.

11. The method of claim 10, wherein providing the gas flow at room temperature comprises preprocessing with a release gas preprocessing element.

12. The method of claim 11, wherein preprocessing comprises removing or reducing humidity from the gas flow.

13. The method of claim 10, further comprising conducting a sample comprising the at least one analyte of interest to the sample concentration element from a sample inlet element prior to trapping the at least one analyte of interest.

14. The method of claim 13, further comprising preprocessing the sample with a sample preprocessing element.

15. The method of claim 10, further comprising conducting the at least one analyte of interest released from the sample concentration element to an analyzer element via a sample outlet element.

* * * * *